Feb. 4, 1964 A. MEILLAND Plant Pat. 2,358
ROSE PLANT
Filed Feb. 5, 1963
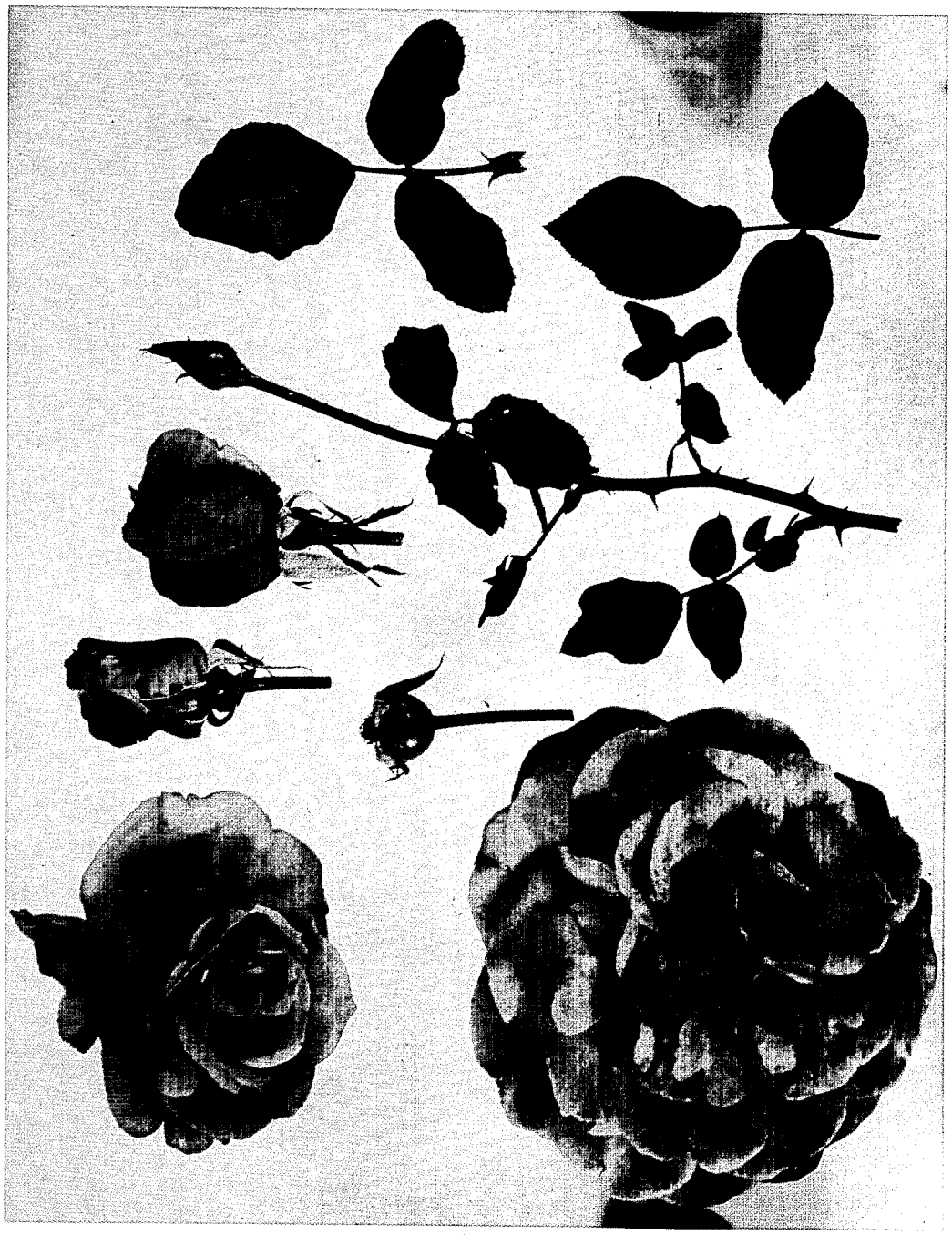
Inventor.
Alain Meilland
By: Robb & Robb
Attorneys.

United States Patent Office

Plant Pat. 2,358
Patented Feb. 4, 1964

2,358
ROSE PLANT

Alain Meilland, Alpes Maritimes, France, assignor to The Conard-Pyle Company, West Grove, Pa., a corporation of Pennsylvania Filed Feb. 5, 1963, Ser. No. 256,487
Claims priority, application France Mar. 9, 1962
1 Claim. (Cl. Plt.—20)

The present invention relates to a new and distinct variety of rose plant of the hybrid tea class, which was originated by me by crossing an unnamed and unpatented seedling derived from a crossing of "Happiness" (U.S. Plant Patent No. 911), known in France as "Rouge Meilland," × "Independence" (U.S. Plant Patent No. 1,036), known in Germany as "Kordes' Sondermeldung," with the variety "Soraya" (unpatented).

The primary objective of this breeding was to produce a new and improved rose variety of the hybrid tea class in which there is combined the vigor and plant habit of the unnamed seedling parent with the floriferousness and flower color of the parent variety "Soraya."

This objective was fully achieved, along with other desirable improvements, as evidenced by the following unique combination of characteristics which are outstanding in the new variety and which distinguish it from its parents, as well as from all other varieties of which I am aware:

(1) A vigorous and well-branched habit of growth;
(2) Good floriferousness;
(3) Large and well-formed blooms of moderate petalage; and
(4) A distinctive and attractive general color tonality of the flowers ranging from Geranium Lake to Carmine, said colors being maintained without significant blueing or fading throughout the life of the flowers.

In comparison with its unnamed seedling parent, the new variety bears blooms of superior size and of lighter and brighter color.

As compared with its pollen parent, "Soraya," the new variety has improved vigor and larger blooms, while the flower color is a lighter shade of orange red than that of the flowers of this parent.

Asexual reproduction of the new variety by budding, as performed in France, and also at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.
Class: Hybrid tea.
Breeding: Seedling.
*Seed parent.*—An unnamed seedling of "Happiness" × "Independence."
*Pollen parent.*—"Soraya."
Propagation: Holds its distinguishing characteristics through succeeding propagations by budding.

*Flower*

Locality where grown and observed: West Grove, Pennsylvania, U.S.A.
Flowers borne: Usually singly, but sometimes several to stem; on stems of medium length and normal strength.
Quantity of bloom: Free, outdoors.
Continuity: Continuous.
Fragrance: Slight. Nature—tea.
Bud:
*Peduncle.*—From medium length to long; medium thickness; erect; medium roughness; with medium number of reddish brown hairs. Color—near Oxblood Red, Plate 00823, overlying Spinach Green, Plate 0960/2.
*Before calyx breaks.*—Size—medium. Form—medium length; pointed; ovoid; with a conspicuous neck; with foliaceous appendages on the surface of the bud; with slender, bristle-like foliaceous parts extending beyond the tip of the bud equal to ¼ or more of its length.
*As calyx breaks.*—Color—Oxblood Red, Plate 00823, sometimes blotched with black.
*As first petal opens.*—Size—medium. Form—medium length; ovoid. Color: outside—near Cardinal Red, Plate 822; inside—Carmine, Plate 21 where first exposed to light, grading to Turkey Red, Plate 721 over remainder of petal.
*Opening.*—Opens up well.
Bloom:
*Size (when fully open).*—Large; from 3½ inches to 4½ inches.
*Petalage.*—Double; from 30 to 35 petals; arranged regularly.
*Form.*—High-centered at first, but becoming cupped; petals being at first loosely rolled outward and remaining loosely rolled outward at maturity.
Petals:
*Texture.*—Medium thickness.
*Appearance.*—Inside—satiny. Outside—shiny.
*Shape.*—Outer petals—obovate. Intermediate petals—obovate. Inner petals—irregular.

This description of a newly opened flower was made from a rose grown outdoors during the month of September at West Grove, Pennsylvania, U.S.A.:

*Color.*—Outer petal: outside surface—near Cherry, Plate 722/2, with point of attachment Empire Yellow, Plate 603; inside surface—near Geranium Lake, Plate 20/1, becoming tinted with China Rose, Plate 024/1 on margins at base of petal, with point of attachment Canary Yellow, Plate 2. Intermediate petal: outside surface—near Cherry Plate 722/2, becoming tinted with Tyrian Rose, Plate 24/2 toward base of petal, with point of attachment Empire Yellow, Plate 603; inside surface—Geranium Lake, Plate 20/1, becoming tinted with Spinel Pink, Plate 0625 toward base of petal, with point of attachment Canary Yellow, Plate 2. Inner petal: outside surface—Cherry, Plate 722/2, becoming tinted with Tyrian Rose, Plate 24/2 toward base of petal, with point of attachment near Sap Green, Plate 62/2; inside surface—Geranium Lake, Plate 20/1, becoming tinted with Spinel Pink, Plate 0625 toward base of petal, with point of attachment Canary Yellow, Plate 2.

This description was made from a rose that was open for three days outdoors during the month of September at West Grove, Pennsylvania, U.S.A.:

*Color.*—Outer petal: outside surface—near China Rose, Plate 024, with point of attachment Empire Yellow, Plate 603; inside surface—Rose Opal, Plate 022, becoming tinted with Rose Madder, Plate 23/1 toward base of petal, with point of attachment Canary Yellow, Plate 2. Inner petal: outside surface—China Rose, Plate 024/1, occasionally streaked with Spinel Red, Plate 0023/3; inside surface—Carmine, Plate 21/1, becoming tinted with Spinel Pink, Plate 0625/1 toward base of petal, with point of attachment Canary Yellow, Plate 2.

*General color effect.*—Newly opened flower—between Geranium Lake, Plate 20/1 and Geranium Lake, Plate 20. 3-days open—Carmine, Plate 21/1.

*Behavior.*—Drop off cleanly; colors assume darker shades during cold weather.

*Flower longevity.*—On bush in garden—4 days in September. Cut roses grown outdoors and kept at living-room temperatures—3 days in September.

*Reproductive Organs*

Stamens: Medium number; arranged irregularly about pistils.

Filaments: Medium number; most with anthers; medium length. Color—Spinel Red, Plate 0023, grading to Oxblood Red, Plate 00823/1 at base.

Anthers: Open at various times; medium size; occasionally an anther fused with a petaloid. Color—Orange Buff, Plate 507.

Pollen: Moderate quantity. Color—gold.

Pistils: Medium number.

Styles: Uneven; from short to medium length; medium heaviness; bunched.

Stigma: Color—yellow.

Ovaries: Some protruding from receptacle.

Hips: Globular; with inconspicuous neck; smooth; walls thick and fleshy. Color—reddish green.

Sepals: Permanent; moderately long; spear-shaped.

*Plant*

Foliage:

*Leaves.*—Usually 3 or 5, but often 7 leaflets; normal abundance; medium size; very leathery.

*Leaflets.*—Shape—oval, with apex acute. Base—obtuse. Margin—simply serrate.

*Color.*—Mature: upper surface—Parsley Green, Plate 00962; under surface—Willow Green, Plate 000862/1. Young: upper surface—near Oxblood Red, Plate 00823; under surface—near Erythrite Red, Plate 0027/1.

*Rachis (the supporting stem of the compound leaf).* — Medium size. Upper side — grooved; hairy. Under side—moderately prickly.

*Stipules.*—Medium length; medium width; with points of medium length turning out at an angle of 45°.

*Disease resistance.*—Comparable to the average variety grown under the same cultural conditions at West Grove, Pennsylvania, U.S.A.

Growth:

*Habit.*—Bushy; much-branched.

*Growth.*—Vigorous.

*Canes.*—Medium heavy.

*Main stems.*—Dull. Color—Spinach Green, Plate 0960/3. Prickles—several; color—light brown. Hairs—none.

*Branches.*—Dull. Color—Spinach Green, Plate 0960/3, overlaid with near Oxblood Red, Plate 00823. Prickles — several; color — brown. Hairs—none.

*New shoots.*—Dull. Color—near Oxblood Red, Plate 00823. Prickles—several; color—Oxblood Red, Plate 00823. Hairs—none.

I claim:

A new and distinct variety of rose plant of the hybrid tea class, substantially as herein shown and described, characterized particularly as to novelty by the unique combination of a vigorous and well-branched habit of growth, good floriferousness, large and well-formed blooms of moderate petalage, and a distinctive and attractive general color tonality of the flowers ranging from Geranium Lake to Carmine, said colors being maintained without significant blueing or fading throughout the life of the flowers.

No references cited.